(12) United States Patent
Pease et al.

(10) Patent No.: US 10,202,430 B2
(45) Date of Patent: Feb. 12, 2019

(54) IGM-MEDIATED RECEPTOR CLUSTERING AND CELL MODULATION

(75) Inventors: Larry R. Pease, Rochester, MN (US); Moses Rodriguez, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 98 days.

(21) Appl. No.: 12/738,774

(22) PCT Filed: Oct. 17, 2008

(86) PCT No.: PCT/US2008/080304
§ 371 (c)(1),
(2), (4) Date: Jun. 28, 2010

(87) PCT Pub. No.: WO2009/052374
PCT Pub. Date: Apr. 23, 2009

(65) Prior Publication Data
US 2010/0291675 A1   Nov. 18, 2010

Related U.S. Application Data

(60) Provisional application No. 60/999,403, filed on Oct. 18, 2007.

(51) Int. Cl.
*A61K 39/00* (2006.01)
*C07K 14/47* (2006.01)

(52) U.S. Cl.
CPC .................. *C07K 14/4726* (2013.01)

(58) Field of Classification Search
None
See application file for complete search history.

(56) References Cited

U.S. PATENT DOCUMENTS

2003/0185827 A1* 10/2003 Rodriguez et al. ........ 424/146.1

FOREIGN PATENT DOCUMENTS

EP   0510949 A2 * 10/1992

OTHER PUBLICATIONS

Donda et al., "In Vivo targeting of an anti-tumor antibody coupled to antigenic MHC class I complexes induces specific growth inhibition and regression of established syngeneic tumor grafts", Cancer Immunol., 3:11,2003 (pp. 1-17).*

Hassan et al., "Prevalence of anti-Fab antibodies in patients with autoimmune and infectious disease", Clin. Exp. Immunol., 89:423-426, 1992.*

* cited by examiner

*Primary Examiner* — Michael Szperka
(74) *Attorney, Agent, or Firm* — Klauber & Jackson LLC (57) ABSTRACT

Materials and methods for using multivalent molecules (e.g., antibodies) to modulate cellular function. A molecule can be targeted to a particular type of cell, either through direct binding to an epitope on the surface of the cell, or through a linker that recognizes both the multivalent molecule and a marker on the cell surface. The invention provides a chimeric polypeptide comprising a first amino acid sequence and a second amino acid sequence, wherein the first amino acid sequence comprises an WIC Class I peptide sequence, and where the second amino acid sequence comprises an epitope to which a multivalent molecule binds, including wherein the multivalent molecule is an IgM antibody, including antibody hIgM22. The invention provides a linker molecule for targeting IgM antibody, including antibody hIgM22, to a cell in the oligodendrocyte lineage.

3 Claims, 4 Drawing Sheets

Specification includes a Sequence Listing.

Vk:
DIQMTQSPSSLSASVGDRVTITCRASQSISSYLNWYQQKP
GKAPKVLIYAASLRSGVPSRFSGSGSGTDFTLTVSSLQPE
DFATYYCQQSYHTPWTFGQGTKVEIK (SEQ ID NO:4)

Ck:
RTVAAPSVFIFPPSDEQLKSGTASVVCLLNNFYPREAKVQ
WKVDNALQSGNSQESVTEQDSKDSTYSLSSTLTLSKADYE
KHKVYACEVTHQGLSSPVTKSFNRGEC (SEQ ID NO:5)

FIGURE 2B

Vh:
QVQLQESGPGLLKPSETLSLTCTVSGGSVSLYYWSWIR
QSPGKEPEWIGYIYSSGSTDYNPSLRSRVTISLDTSNNR
FSLNLRSVTAADTAVYWCARSASIRGWFDPWGQGTLV
TVSS (SEQ ID NO:6)

CH1:
GSASAPTLFPLVSCENSPSDTSSVAVGCLAQDFLPDSIT
FSWKYKNNSDISSTRGFPSVLRGGKYAATSQVLLPSKD
VMQGTDEHVVCKVQHPNGNKEKNVPLP (SEQ ID NO:7)

CH2:
VIAELPPKVSVFVPPRDGFFGNPRKSKLICQATGFSPRQI
QVSWLREGKQVGSGVTTDQVQAEAKESGPTTYKVTST
LTIKESDWLSQSMFTCRVDHRGLTFQQNASSMCVP
(SEQ ID NO:8)

CH3:
DQDTAIRVFAIPPSFASIFLTKSTKLTCLVTDLTTYDSVTIS
WTRQNGEAVKTHTNISESHPNATFSAVGEASICEDDWN
SGERFTCTVTHTDLPSPLKQTISRPK (SEQ ID NO:9)

CH4:
GVALHRPDVYLLPPAREQLNLRESATITCLVTGFSPADV
FVQWMQRGQPLSPEKYVTSAPMPEPQAPGRYFAHSIL
TVSEEEWNTGETYTCVVAHEALPNRVTERTVDKSTGKP
TLYNVSLVMSDTAGTCY (SEQ ID NO:10)

GACATCCAGATGACCCAGTCTCCATCCTCCTTGTCTGCGTCTG
TAGGAGACAGAGTCACCATCACTTGCCGGGCAAGTCAGAGTA
TTAGTAGTTATCTAAATTGGTATCAGCAGAAACCAGGGAAAGC
CCCTAAGGTCCTGATCTATGCTGCATCCACTTTGCGAAGTGG
GGTCCCGTCAAGGTTCAGTGGCAGTGGATCTGGGACAGATTT
CACTCTCACCGTCAGCAGTCTGCAACCTGAAGATTTTGCAACT
TACTACTGTCAACAGAGTTACCATACCCCGTGGACGTTCGGTC
AGGGGACCAAGGTGGAAATCAAACGAACTGTGGCTGCAC (SEQ ID NO:11)

Vh:

CAGGTGCAGCTGCAGGAGTCGGGTCCAGGACTGCTGAAGCC
TTCGGAGACCCTGTCCCTCACATGCACTGTCTCTGGTGGCTC
CGTCAGTCTTTACTACTGGAGCTGGATCCGGCAGTCCCCAGG
GAAGGAACCGGAGTGGATTGGATATATCTATTCCAGTGGAAG
CACCGATTACAACCCTTCCCTCAGGAGTCGAGTCACCATATCA
CTGGACACGTCAAACAACCGGTTTTCCCTAAACCTGAGGTCTG
TGACCGCCGCAGATACAGCGGTCTATTGGTGTGCGAGAAGTG
CGTCAATTAGGGGCTGGTTCGACCCCTGGGGCCAGGGAACC
CTGGTCACCGTCTCCTCAGGGAGTGCATCCGCC (SEQ ID NO:12)

IGM-MEDIATED RECEPTOR CLUSTERING AND CELL MODULATION

CROSS-REFERENCE TO RELATED APPLICATIONS

This application claims benefit of priority from U.S. Provisional Application Ser. No. 60/999,403, filed on Oct. 18, 2007.

STATEMENT AS TO FEDERALLY SPONSORED RESEARCH

This invention was made with government support under grant no. CA096859 awarded by the National Cancer Institute. The government has certain rights in the invention.

TECHNICAL FIELD

This document relates to materials and methods for using multivalent molecules (e.g., antibodies) to modulate cellular function.

BACKGROUND

Dendritic cells (DC) are efficient antigen-presenting cells (APC). These cells express class I and class II major histocompatibility complex (MHC) peptide-presenting molecules on their cell surfaces, along with a series of costimulatory molecules (Banchereau and Steinman (1998) *Nature* 392:245-252). Naive T cells express receptors for these DC ligands. Following recognition of peptide-antigen presented in the context of class I or class II molecules, the structure of the T cell membrane is reorganized, bringing together the elements of the T cell receptor with other cell-surface molecules, including the co-receptors CD4 or CD8 and the costimulatory receptors CD28 and CTLA-4 (Monks et al. (1998) *Nature* 395:82-86; and Wulfing and Davis (1998) *Science* 282:2266-2269). Interactions within the newly formed macromolecular complexes determine the outcome of inductive events transduced into T cells by DC.

DC reside in a variety of tissues and display distinct tissue-associated phenotypes (Strunk et al. (1997) *J. Exp. Med.* 185:1131-1136; Caux et al. (1996) *J. Exp. Med.* 184:695-706; Wu et al. (1996) *J. Exp. Med.* 184:903-911; and Vremec et al. (1992) *J. Exp. Med.* 176:47-58). The relationships among the cell lineages of these different subsets of cells are not firmly established. A large body of work has emerged focusing on DC generated in vitro from bone marrow or blood precursors (Mayordomo et al. (1995) *Nat. Med.* 1:1297-1302; Nonacs et al. (1992) *J. Exp. Med.* 176:519-529; Steinman and Witmer (1978) *Proc. Natl. Acad. Sci. USA* 75:5132-5136; and Young and Steinman (1990) *J. Exp. Med.* 171:1315-1332). The cells generated in vitro express high levels of class I antigens and the series of costimulatory ligands associated with endogenous DC (Fagnoni et al. (1995) *Immunology* 85:467-474; and Banchereau et al. (2000) *Annu. Rev. Immunol.* 18:767-811). Importantly, they are able to efficiently activate naive T cells, a function that is the signature of the DC.

Decavalent IgM antibodies display measurable binding avidity to antigens, even though binding affinity may be low. The multivalent structure of pentameric IgM provides the potential for cross-linking cell surface targets, endowing the soluble antibodies with biological potential not normally associated with immune function. One such IgM antibody, which is referred to herein as B7-DC XAb but also has been called sHIgM12, rHIgM12, and Lym12, was originally isolated from a Waldenstrom's macroglobulinemia patient, and described in U.S. Ser. No. 10/983,104 (incorporated herein by reference in its entirety).

SUMMARY

As described herein, IgM antibodies and other multivalent molecules can be used to cluster and cap cell surface molecules on a variety of cell types, resulting in intracellular signaling and modulation of the targeted cells' functions. These methods takes advantage of certain IgM molecules' ability to bind with very low affinity to sets of endogenous ligands. Cell function can be modulated by targeting an IgM to a particular cell type via (1) a typical antibody interaction with an antigen normally expressed on the targeted cell, (2) a transgenic molecule expressed on the cell surface containing an epitope recognized by the IgM, or (3) a linker construct (e.g., a peptide or an antibody) with the ability to bind to the IgM and to a cell surface protein specific to the given cell type. Once the IgM has been recruited to the cell surface, its low affinity interaction with other endogenous ligands can result in receptor and cell surface molecule clustering, initiating intracellular signaling and modulating cell functions.

In one aspect, this document features a method for targeting a multivalent molecule to a cell, comprising: (a) contacting the cell with a linker molecule, wherein the linker molecule includes (i) an amino acid sequence comprising an epitope to which the multivalent molecule specifically binds and (ii) an amino acid sequence that binds specifically to a marker on the outer surface of the cell; and (b) contacting the cell with the multivalent molecule. The multivalent molecule can be an antibody (e.g., an IgM antibody). The linker molecule can consist of a polypeptide. The linker molecule can be a chimeric antibody.

In another aspect, this document features a method for targeting a multivalent molecule to a cell, comprising: (a) contacting the cell with a nucleic acid encoding a polypeptide, wherein the polypeptide includes (i) an amino acid sequence that directs the polypeptide to the cell's plasma membrane and (ii) an amino acid sequence comprising an epitope to which the multivalent molecule specifically binds; (b) culturing the cell under conditions in which the polypeptide is expressed and localized to the plasma membrane such that the epitope is located on the exterior of the cell; and (c) contacting the cell with the multivalent molecule. The multivalent molecule can be an antibody (e.g., an IgM antibody).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 depicts the amino acid sequences of B7-DC XAb.

DETAILED DESCRIPTION

Described herein are multivalent molecules that can activate the function of particular cell types. This work has implications for treatment of a wide variety of human diseases. For example, monoclonal IgM therapeutic antibodies (MTAbs) have been identified that can activate cells in the oligodendrocyte lineages, inducing, e.g., immune modulation and remyelination of denuded axons (Warrington et al. (2000) Proc. Natl. Acad. Sci. U.S.A. 97:6820-6825; and Miller and Rodriguez (1995) J. Immunol. 154: 2460-2469). A remarkable feature of MTAbs is their tendency to bind to and activate homologous cells in rodents and humans (Warrington et al., supra), facilitating the use of animal models in preclinical studies. These antibodies are present in the normal human repertoire, and can be identified in patients with monoclonal gammopathies.

MTAbs can function at very low concentrations, similar to what is observed with conventional growth factors (Warrington et al. (2007) J. Neurosci. Res. 85:967-976). While the clinical application of growth factors has been hampered by their short half life and difficulty of delivery, these obstacles can be overcome by MTAbs. IgM antibodies are natural blood products and have half lives in humans of days. In addition, these molecules activate cells to perform inherent "luxury" functions. For example, MTAbs can activate oligodendrocytes to make new myelin wraps around axons (Warrington et al. (2000), supra; and Miller et al. (1994) J. Neurosci. 14:6230-6238). MTAbs thus represent a new class of clinically useful reagent which may have wide applicability.

The mechanism by which MTAbs activate targeted cells has remained obscure, as cell surface molecules bound by these antibodies are not well defined. It has been demonstrated that a human MTAb, rHIgM22, an antibody that induces myelin repair in models of multiple sclerosis, can activate cells. Antibody rHIgM22 was deposited in the American Type Culture Collection (ATCC; 10801 University Boulevard, Manassas, Va. 20110-2209) on Sep. 28, 2007, and assigned Patent Deposit Designation PTA-8671. Therapeutic antibodies can rapidly induce formation of multi-molecular caps on the surface of targeted cells, recruit signaling molecules that are known to control important cellular functions, and activate a series of intracellular signals in response.

MTAbs can modulate immune responsiveness and oligodendrocyte maturation by targeting cells in situ and inducing preprogrammed cellular functions. MTAbs capable of inducing anti-tumor immunity, blocking allergic airway inflammation, and inducing remyelination of denuded axons can employ a common cellular activation mechanism. For example, these antibodies can cross-link cell surface molecules and assemble macromolecular signaling complexes by recruiting receptor and adapter molecules into clusters, thereby activating key signaling pathways. Additional MTAbs that target cells specifically throughout the body can be identified within the normal human antibody repertoire, providing the basis for the development of novel therapeutic approaches to treat disease.

Figure 1:
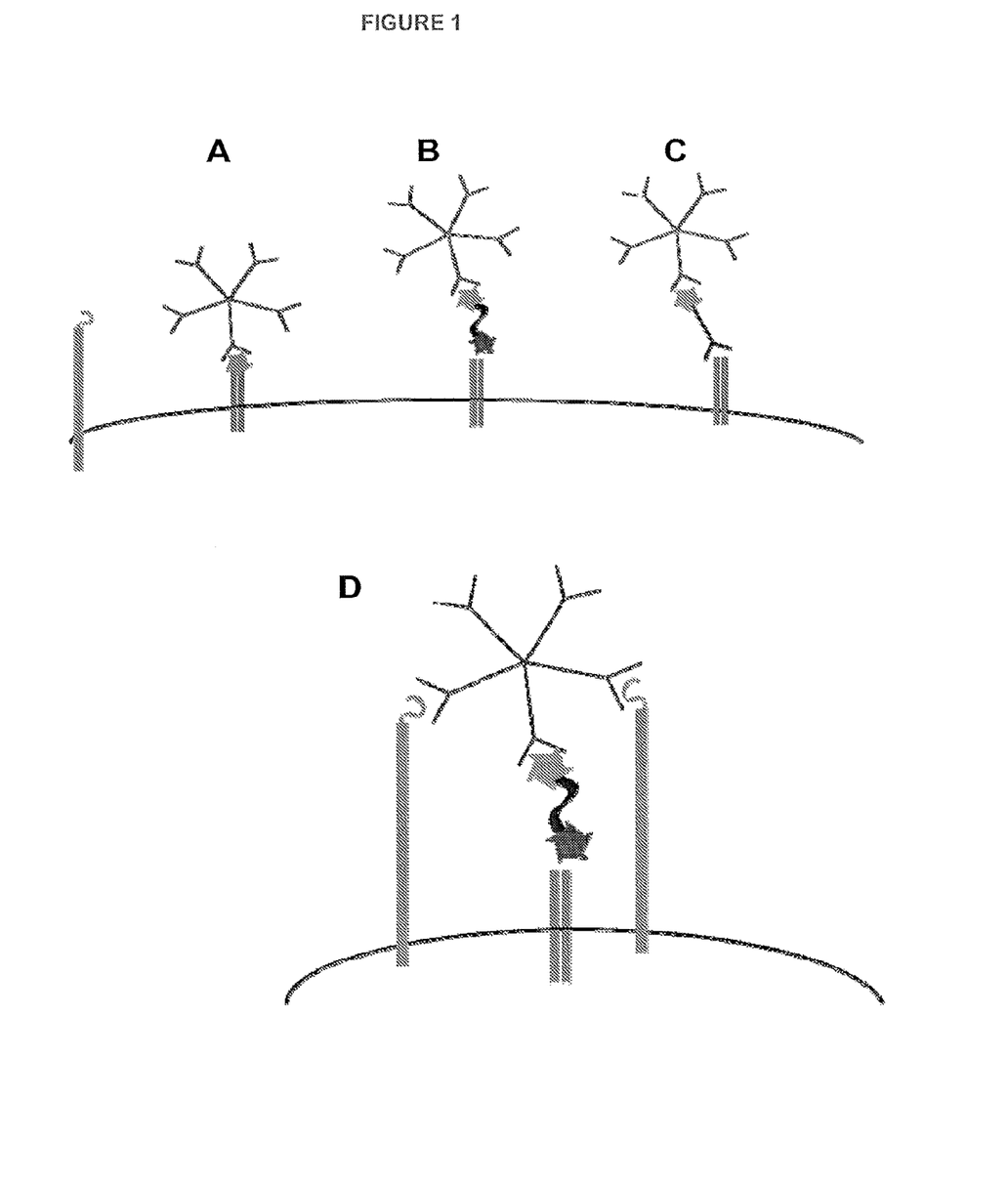
FIG. 1 is a schematic showing IgM binding to a cell surface receptor. IgM antibodies can interact with cells via transgenic molecules expressed on the cell surface that contain an epitope recognized by the IgM (FIG. 1A), or a linker peptide (FIG. 1B) or antibody (FIG. 1C) having the ability to bind to the IgM and to a cell surface protein specific to the given cell type. Once recruited to the cell surface, the interaction of the IgM with other endogenous ligands can result in receptor and cell surface molecule clustering (FIG. 1D).

As described herein, IgM antibodies or other multivalent molecules can be used to cluster and cap cell surface molecules on a variety of cell types, resulting in intracellular signaling and modulation of the targeted cells' functions. These methods take advantage of certain IgM molecules' ability to bind with very low affinity to sets of endogenous ligands. In some embodiments, cell function can be modulated by targeting the IgM to a particular cell type via a "typical" antibody interaction with an antigen normally expressed on the targeted cell, or a transgenic molecule expressed on the cell surface containing an epitope recognized by the IgM (e.g., as depicted in FIG. 1A). In some cases, an IgM antibody can be targeted to a particular cell type via a linker molecule. A linker can interact with both an IgM via a mimetope recognized the IgM, and with a cell surface molecule specific to the given cell type. A linker can be, for example, a specially designed peptide or nucleic acid (FIG. 1B), or an antibody linked to a mimetope recognized by IgM (FIG. 1C). Once the IgM has been recruited to the cell surface, its low affinity interaction with other endogenous ligands can result in clustering/capping of the receptors, cell surface molecules, and adapter proteins (FIG. 1D), initiating intracellular signaling and modulating cell functions.

This ability to target a "generic" MTAb to a variety of different cell types using a linker can have a number of advantages. For example, because every IgM does not have sufficient affinity to bind effectively to endogenous ligands, a single MTAb can be used against a variety of different cell types. This can be especially useful if an IgM is identified that has no affinity for a specific receptor or a particular cell type. In addition, other types of multivalent molecules (e.g., tetramers, specially designed beads, and other constructs) can be designed to bind a specific linker and to have low affinity for endogenous ligands found on all cell types.

Linker polypeptides can be designed using any suitable means, including phage display. Such methods can allow the design of linkers specific to cell types where a cell-type specific receptor/surface molecule has not been identified. Moreover, linker polypeptides can be designed using very small peptides, such that the full construct is about 15 to about 40 amino acids in length (e.g., about 20 amino acids, about 25 amino acids, about 30 amino acids, about 35 amino acids, or about 40 amino acids in length). Such linkers can be synthesized using standard techniques.

Further, the ability to target MTAbs to different cell types using a linker system can have enormous therapeutic potential. For example, a linker can be used to target an antibody specifically to a $T_{reg}$ cell or to a stem cell, enhancing or inhibiting its activation for therapeutic purposes. For example, a stem cell could be activated using an MTAb and a linker to promote differentiation either in vivo or ex vivo, providing a means for creating more differentiated stem cells for a variety of treatments (e.g., cardiac stem cells for treating myocardial infarction, or pancreatic islet cells for treating diabetes).

In addition, the ability to use a linker can be combined with other uses of therapeutic antibodies, such that the antibodies have multiple effects.

Polypeptides and Antibodies

The molecules provided herein typically are polypeptides, and antibodies can be particularly useful (see below), but other multivalent molecules that can bind and cross-link molecules on the surface of cells also can function in this capacity. Examples of such molecules include, without limitation, multivalent RNA or DNA aptamers.

As used herein, a polypeptide is an amino acid chain, regardless of length or post-translational modification (e.g., phosphorylation or glycosylation). A polypeptide can contain an amino acid sequence that is similar to the amino sequence of B7-DC AXb, for example. A polypeptide can contain, e.g., an amino acid sequence that is at least 80.0% identical (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, 99.9%, from 95% to 99.9%, from 96% to 99.9%, from 97% to 99.9%, or from 98% to 99.9% identical) to the amino acid sequence set forth in SEQ ID NO 4 or SEQ ID NO:6. In some embodiments, a polypeptide can further contain an amino acid sequence that is at least 80.0% identical (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, 99.9%, from 95% to 99.9%, from 96% to 99.9%, from 97% to 99.9%, or from 98% to 99.9% identical) to the amino acid sequence set forth in SEQ ID NO:5, SEQ ID NO:7, SEQ ID NO:8, SEQ ID NO:9, or SEQ ID NO:10. Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence.

To determine percent sequence identity, a target nucleic acid or amino acid sequence is compared to the identified nucleic acid or amino acid sequence using the BLAST 2 Sequences (B12seq) program from the stand-alone version of BLASTZ containing BLASTN version 2.0.14 and BLASTP version 2.0.14. This stand-alone version of BLASTZ can be obtained from Fish & Richardson's web site or the U.S. government's National Center for Biotechnology Information web site. Instructions explaining how to use the B12seq program can be found in the readme file accompanying BLASTZ.

B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\B12seq c:\seq1.txt -j c:\seq2.txt -p blastn -o c:\output.txt -q -1 -r 2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:4), or by an articulated length (e.g., 100 consecutive nucleotides or amino acid residues from a sequence set forth in an identified sequence), followed by multiplying the resulting value by 100. For example, a nucleic acid sequence that has 98 matches when aligned with the sequence set forth in SEQ ID NO:4 is 92.5 percent identical to the sequence set forth in SEQ ID NO:4 (i.e., 98/106*100=92.5). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It is also noted that the length value will always be an integer.

The amino acid sequences of the polypeptides provided herein can have substitutions, deletions, or additions with respect to the amino acid sequences set forth in SEQ ID NOS:4 and 6. A polypeptide having an amino acid sequence that is modified (e.g., by substitution) with respect to SEQ ID NO:4 and/or SEQ ID NO:6 can have substantially the same or improved qualities as compared to a polypeptide containing the amino acid sequence identical to that set forth in SEQ ID NO:4 and SEQ ID NO:6. A substitution can be a conserved substitution. As used herein, a "conserved substitution" is a substitution of an amino acid with another amino acid having a similar side chain. A conserved substitution typically can be a substitution with an amino acid that makes the smallest change possible in the charge of the amino acid or size of the side chain of the amino acid (alternatively, in the size, charge or kind of chemical group within the side chain) such that the overall peptide essentially retains its spatial conformation but has altered biological activity. Examples of conserved changes include, without limitation, Asp to Glu, Asn or Gln; His to Lys, Arg or Phe; Asn to Gln, Asp or Glu, and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cysteine, tyrosine, asparagine and glutamine having uncharged polar side chains; aspartate and glutamate having acidic side chains; and lysine, arginine, and histidine having basic side chains (see, e.g., Stryer, Biochemistry ($2^{nd}$ edition) W. H. Freeman and Co. San Francisco (1981), pp. 14-15; and Lehninger, Biochemistry ($2^{nd}$ edition, 1975), pp. 73-75). Conservative substitutions can include substitutions made within these groups.

Molecules provided herein can be antibodies. The terms "antibody" and "antibodies" encompass intact molecules as well as fragments thereof that can bind to a particular antigen. Antibodies can be polyclonal antibodies, monoclonal antibodies, humanized or chimeric antibodies, single chain Fv antibody fragments, Fab fragments, and F(ab)$_2$ fragments. Polyclonal antibodies are heterogeneous populations of antibody molecules that are specific for a particular antigen, while monoclonal antibodies are homogeneous populations of antibodies to a particular epitope contained within an antigen.

An antibody can be of any immunoglobulin (Ig) class, including IgM, IgA, IgD, IgE, and IgG, and any subclass thereof. Antibodies of the IgM class (e.g., B7-DC XAb) typically are pentavalent and can be particularly useful. Immune complexes containing Ig molecules that are cross-linked (e.g., cross-linked IgG) and are thus multivalent also can be particularly useful.

As used herein, an "epitope" is a portion of an antigenic molecule to which an antibody binds. Antigens can present more than one epitope at the same time. For polypeptide antigens, an epitope typically is about four to six amino acids in length, and can include modified (e.g., phosphorylated or glycosylated) amino acids. Two different immunoglobulins can have the same epitope specificity if they bind to the same epitope or set of epitopes.

Polyclonal antibodies are contained in the sera of immunized animals. Monoclonal antibodies can be prepared using, for example, standard hybridoma technology. In particular, monoclonal antibodies can be obtained by any technique that provides for the production of antibody molecules by continuous cell lines in culture as described, for example, by Kohler et al. (1975) *Nature* 256:495-497, the human B-cell hybridoma technique of Kosbor et al. (1983) *Immunology Today* 4:72, and Cote et al. (1983) *Proc. Natl. Acad. Sci. USA* 80:2026-2030, and the EBV-hybridoma technique of Cole et al., *Monoclonal Antibodies and Cancer Therapy*, Alan R. Liss, Inc. pp. 77-96 (1983). A hybridoma producing monoclonal antibodies can be cultivated in vitro or in vivo.

Antibodies also can be isolated from, for example, the serum of an individual. The B7-DC XAb antibody, for example, was isolated from human serum as described in U.S. Pat. No. 7,052,694. Suitable methods for isolation include purification from mammalian serum using techniques that include, for example, chromatography.

Antibodies also can be produced by, for example, immunizing host animals (e.g., rabbits, chickens, mice, guinea pigs, or rats) with an immunogen (e.g., an antigen or epitope). An immunogen can be produced recombinantly, by chemical synthesis, or by purification of the native protein, and then used to immunize animals by injection of the polypeptide. Adjuvants can be used to increase the immunological response, depending on the host species. Suitable adjuvants include Freund's adjuvant (complete and incomplete), mineral gels such as aluminum hydroxide, surface active substances such as lysolecithin, pluronic polyols, polyanions, peptides, oil emulsions, keyhole limpet hemocyanin (KLH), and dinitrophenol. Standard techniques can be used to isolate antibodies generated in response to the immunogen from the sera of the host animals.

Antibodies such as B7-DC XAb also can be produced recombinantly. The amino acid sequence (e.g., the partial amino acid sequence) of an antibody can be determined by standard techniques, and a cDNA encoding the antibody or a portion of the antibody can be isolated from the serum of the subject (e.g., the human patient or the immunized host animal) from which the antibody was originally isolated. The cDNA can be cloned into an expression vector using standard techniques. The expression vector then can be transfected into an appropriate host cell (e.g., a Chinese hamster ovary cell, a COS cell, or a hybridoma cell), and the antibody can be expressed and purified. See, for example, U.S. Ser. No. 10/983,104. Antibody fragments that have specific binding affinity for an antigen also can be generated by techniques such as those disclosed above. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al. (1989) *Science* 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778. Such fragments can be rendered multivalent by, for example, biotinylation and cross-linking, thus generating antibody fragments that can cross-link a plurality of B7-DC polypeptides.

Nucleic Acids, Vectors, and Host Cells

Nucleic acids encoding polypeptides and antibodies also are provided herein.

The term "nucleic acid" refers herein to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids include, for example, cDNAs encoding antibody light and heavy chains.

An "isolated nucleic acid" refers to a nucleic acid that is separated from other nucleic acid molecules that normally flank one or both sides of the nucleic acid in the genome in which it is normally found. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in its naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Figure 2A:
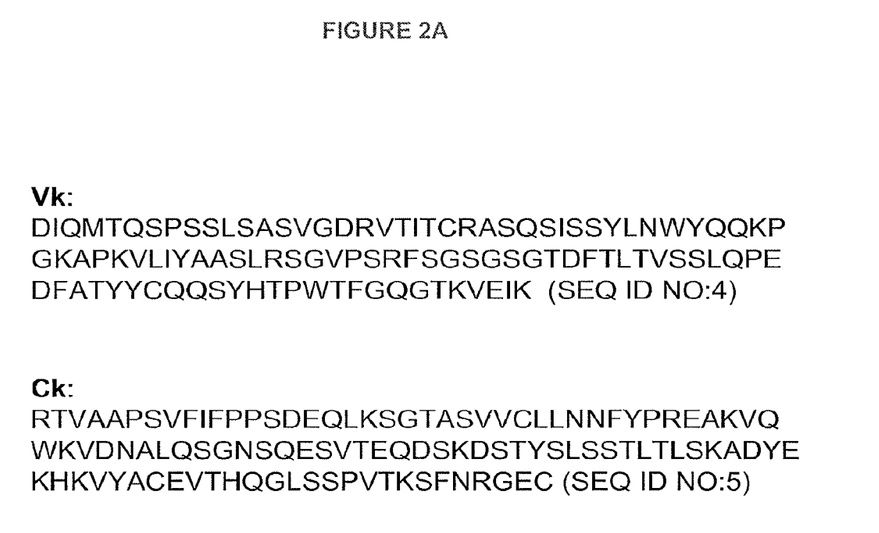
FIG. 2A shows the variable (Vk) and constant (Ck) domains (SEQ ID NOS:4 and 5, respectively) of the B7-DC XAb light chain.
Figure 2B:
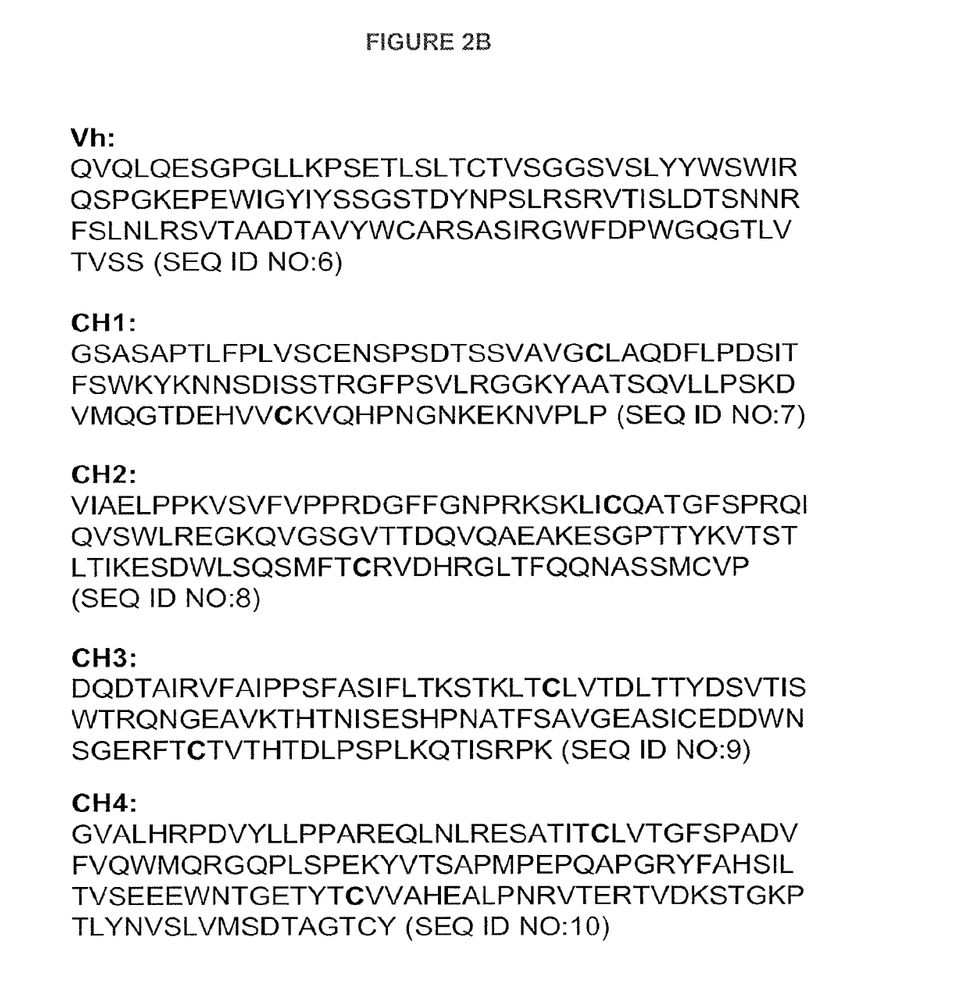
FIG. 2B shows the variable (Vh) and constant (CH1, CH2, CH3, CH4) domains (SEQ ID NOS:6, 7, 8, 9, and 10, respectively) of the sHIgM12 heavy chain.
Figure 3:
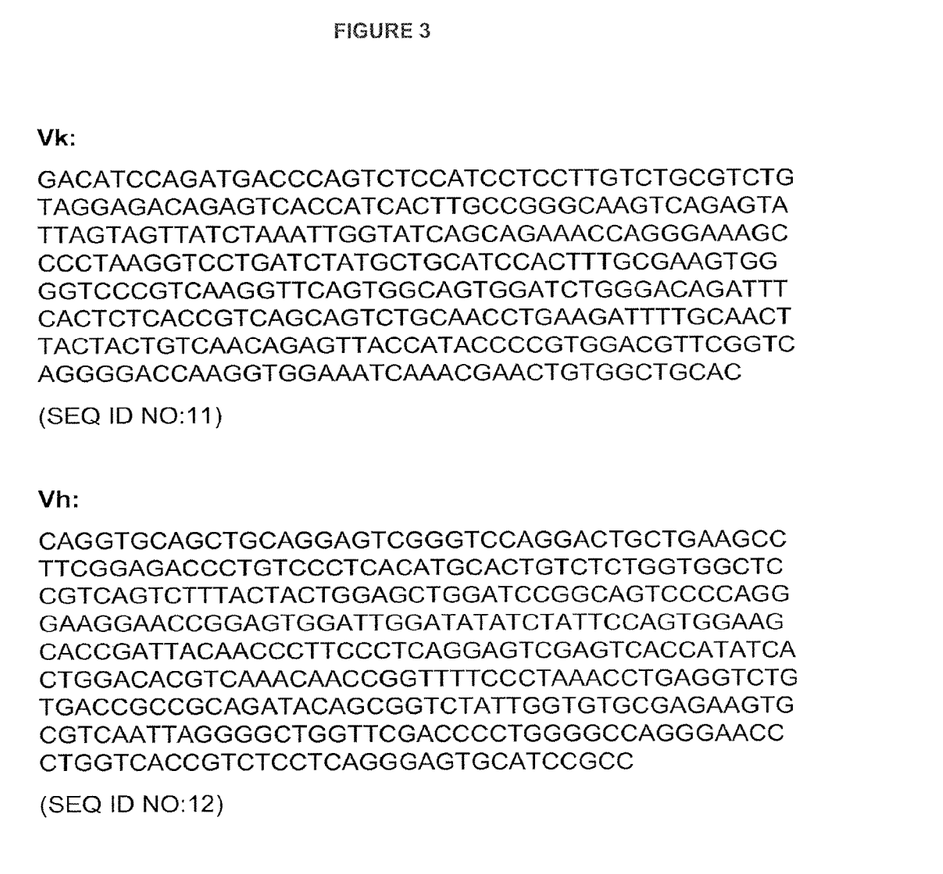
FIG. 3 depicts the nucleic acid sequences of B7-DC XAb. Nucleic acids sequences encoding the Vk and Vh domains (SEQ ID NOS:11 and 12, respectively) B7-DC XAb.

The isolated nucleic acids disclosed herein can encode polypeptides as described herein. For example, an isolated nucleic acid can encode a polypeptide containing an amino acid sequence that is similar or identical to an amino acid sequence found in the variable or constant regions of B7-DC XAb (e.g., SEQ ID NOS:4, 5, 6, 7, 8, 9, 10, 11, and 12, shown in FIGS. 2A, 2B, and 3). In some embodiments, a nucleic acid can encode a polypeptide containing an amino acid sequence that is at least 80.0% identical (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8, 99.9%, from 95% to 99.9%, from 96% to 99.9%, from 97% to 99.9%, or from 98% to 99.9% identical) to the amino acid sequence set forth in SEQ ID NO:4 or SEQ ID NO:6. The encoded polypeptide can further contain an amino acid sequence that is at least 80.0% identical (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, 99.9%, from 95% to 99.9%, from 96% to 99.9%, from 97% to 99.9%, or from 98% to 99.9% identical) to the amino acid sequence set forth in SEQ ID NO:5, SEQ ID NO:7, SEQ ID NO:8, SEQ ID NO:9, or SEQ ID NO:10. In some cases, an isolated nucleic acid can contain a nucleotide sequence that is at least 80.0% identical (e.g., 80.0%, 85.0%, 90.0%, 95.0%, 97.0%, 97.5%, 98.0%, 98.5%, 99.0%, 99.1%, 99.2%, 99.3%, 99.4%, 99.5%, 99.6%, 99.7%, 99.8%, 99.9%, from 95% to 99.9%, from 96% to 99.9%, from 97% to 99.9%, or from 98% to 99.9% identical) to the nucleotide sequence set forth in SEQ ID NO:11 or SEQ ID NO:12. The method for determining percent sequence identity is provided above.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid molecule encoding an antibody. Isolated nucleic acids also can be chemically synthesized, either as a single nucleic acid molecule (e.g., using automated DNA synthesis in the 3' to 5' direction using phosphoramidite technology) or as a series of polynucleotides. For example, one or more pairs of long polynucleotides (e.g., >100 nucleotides) can be synthesized that contain the desired sequence, with each pair containing a short segment of complementarity (e.g., about 15 nucleotides) such that a duplex is formed when the polynucleotide pair is annealed. DNA polymerase is used to extend the polynucleotides, resulting in a single, double-stranded nucleic acid molecule per polynucleotide pair.

Vectors containing nucleic acids such as those described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In the expression vectors provided herein, a nucleic acid (e.g., a nucleic acid encoding the light and/or heavy chains of an antibody such as B7-DC XAb) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence. Expression vectors thus can be useful to produce antibodies as well as other multivalent molecules.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

Host cells containing vectors also are provided. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* (2$^{nd}$ edition), Cold Spring Harbor Laboratory, New York (1989), and reagents for transformation and/or transfection are commercially available (e.g., LIPOFECTIN® (Invitrogen); FUGENE (Roche, Indianapolis, Ind.); and SUPERFECT® (Qiagen, Valencia, Calif.)).

Also provided herein are cells contacted in vitro with a multivalent polypeptide (e.g., an IgM antibody) as described herein.

Compositions

The molecules described herein (e.g., antibodies such as B7-DC XAb and nucleic acids encoding linkers or transgenic receptors) can be incorporated into compositions, as can isolated cells that have been contacted with one or more molecules as described herein. Compositions provided herein also can contain a molecule (e.g., a polypeptide) that is immobilized on a solid substrate, such as a bead. The compositions can be administered to a subject in order to modulate cellular function.

Methods for formulating and subsequently administering therapeutic compositions are well known to those skilled in the art. Dosages typically are dependent on the responsiveness of the subject to the molecule, with the course of treatment lasting from several days to several months, or until a suitable immune response is achieved. Persons of ordinary skill in the art routinely determine optimum dosages, dosing methodologies and repetition rates. Optimum dosages can vary depending on the relative potency of an antibody, and generally can be estimated based on the $EC_{50}$ found to be effective in in vitro and/or in vivo animal models. Dosage typically is from 0.01 µg to 100 g per kg of body weight (e.g., from 1 µg to 100 mg, from 10 µg to 10 mg, or from 50 µg to 500 µg per kg of body weight). Compositions containing the molecules provided herein may be given once or more daily, weekly, monthly, or even less often.

In addition to the molecules provided herein, the compositions described herein further can contain antigens that will elicit a specific immune response. Suitable antigens include, for example, polypeptides or fragments of polypeptides expressed by tumors and pathogenic organisms. Killed viruses and bacteria, in addition to components of killed viruses and bacteria, also are useful antigens. Such antigens can stimulate immune responses against tumors or pathogens.

The molecules (e.g., antibodies, other polypeptides, or nucleic acids) can be admixed, encapsulated, conjugated or otherwise associated with other molecules, molecular structures, or mixtures of compounds such as, for example, liposomes, receptor targeted molecules, or oral, topical or other formulations for assisting in uptake, distribution and/or absorption.

In some embodiments, a composition can contain a molecule provided herein in combination with a pharmaceutically acceptable carrier. Pharmaceutically acceptable carriers are pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing molecules provided herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous (i.v.) drip); oral; topical (e.g., transdermal, sublingual, ophthalmic, or intranasal); or pulmonary (e.g., by inhalation or insufflation of powders or aerosols). Administration can be rapid (e.g., by injection) or can occur over a period of time (e.g., by slow infusion or administration of slow release formulations). For administration to the central nervous system, antibodies can be injected or infused into the cerebrospinal fluid, typically with one or more agents capable of promoting penetration across the blood-brain barrier.

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Molecules featured herein can encompass any pharmaceutically acceptable salts, esters, or salts of such esters, or any other compound which, upon administration to a subject, is capable of providing (directly or indirectly) the biologically active metabolite or residue thereof. Accordingly, for example, this document provides pharmaceutically acceptable salts of molecules such as antibodies, prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the antibodies useful in methods provided herein (i.e., salts that retain the desired biological activity of the parent antibodies without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions described herein, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the other components within the compositions.

Pharmaceutical formulations as disclosed herein, which can be presented conveniently in unit dosage form, can be prepared according to conventional techniques well known in the pharmaceutical industry. Such techniques include the step of bringing into association the active ingredients (i.e., the antibodies) with the desired pharmaceutical carrier(s). Typically, the formulations can be prepared by uniformly and intimately bringing the active ingredients into association with liquid carriers or finely divided solid carriers or both, and then, if necessary, shaping the product. Formulations can be sterilized if desired, provided that the method of sterilization does not interfere with the effectiveness of the molecules(s) contained in the formulation.

Methods

This document provides methods for targeting multivalent molecules to a particular cell type. Such methods can include, for example, contacting a cell with a multivalent polypeptide (e.g., an IgM antibody) that can bind specifically to a particular epitope. In some embodiments, the epitope can be present on the surface of the cell. In such cases, the epitope can be contained within a native polypeptide that is expressed on the cell surface, or can be a mimetope contained within a transgenic polypeptide that is expressed on the cell surface. In the latter case, the method can include contacting the cell with a nucleic acid encoding the transgenic polypeptide, such that the transgenic polypeptide is expressed on the cell surface. In some embodiments, the epitope can be included in a linker molecule (e.g., a polypeptide or antibody) that interacts with both the multivalent molecule and with a cell surface molecule. In such cases, the method can include contacting the cell with the linker or with a nucleic acid encoding the linker.

The methods provided herein can be used to modulate the function(s) of the cells to which the multivalent molecules and other components are administered. In some embodiments, for example, a multivalent molecule (e.g., an antibody such as B7-DC XAb) or a composition containing the multivalent molecule or a nucleic acid encoding the molecule can be administered to a mammal (e.g., a dog, a cat, a horse, a cow, a rabbit, a rat, a mouse, or a human). As described above, the molecule(s) or composition can be administered using any suitable systemic or local method. Systemic methods of administration include, without limitation, oral, topical, or parenteral administration, as well as administration by injection. Local methods of administration include, for example, direct injection into a tumor.

Methods also are provided that include contacting an isolated cell (e.g., a dendritic cell, or any other type of cell) in vitro with a multivalent polypeptide (e.g., an IgM antibody) as described above, and administering the cell to a subject.

The invention will be further described in the following examples, which do not limit the scope of the invention described in the claims.

EXAMPLES

Example 1—Materials and Methods

Mice:

C57BL/6J, B6.129s4-CD80-/-CD86-/-, CNCr.129P2-Cd40tm1Kik/J, and B6.12952-IL6tm1Kopf/J mice, 6-8 weeks old, were obtained from Jackson Laboratories (Bar Harbor, Me.). Class II knock out mice (L. Madsen et al. (1999) *Proc. Natl. Acad. Sci. USA* 96:10338-10343) were a gift from Dr. Chella David, Mayo Clinic. TREM-2 knock out mice (Turnbull et al. (2006) *J. Immunol.* 177:3520-3524), bred in the mouse colony at Washington University School of Medicine, St. Louis, Mo., were provided by Dr. Marco Colonna. Pregnant rats were purchased from Harlan Sprague (Indianapolis, Ind.). All animals were maintained at the Mayo Clinic animal facility for at least one week prior to use.

Reagents:

Appropriate fluorophore labeled antibodies against murine I-A$^b$ (25-9-17), murine class II specific IgM (25-9-3), APC labeled anti-mouse CD11c (HL3) FITC labeled anti-human class II (TU39), FITC labeled anti-human CD28 (CD28.2), APC labeled anti-human CD28 (CD28.2), PE labeled anti-human CD4 (RPA-T4) and PE labeled anti-human HLA A, B, C (G46-2.6) were purchased from BD PharMingen (San Jose, Calif.). Appropriate fluorophore labeled antibodies against mouse class II (M5/114.15.2), CD80 (16.10A1), CD86 (GL-1), CD11c (N418), CD40 (IC 10), APC labeled antibody against human DR (LN3), PE labeled anti-human CD80 (2D10.4), CD86 (IT2.2), murine B7-DC specific IgG antibody (TY25), and human B7-DC IgG antibody (MIH18) were purchased from eBioscience (San Diego, Calif.). All secondary appropriately fluorophore labeled F(ab)$^2$ fragment antibodies were obtained from Jackson Immunoresearch (Westgrove, Pa.). An IgM antibody (28-13-3) specific for mouse class I H-2 K$^b$ was obtained from a hybridoma cell line from ATCC (HB-41) (Manassas, Va.). Antibodies against the C terminal portion of NF-κB (sc372) and the protein kinase Syk (4D10) were obtained from Santa Cruz Biotechnology (Santa Cruz, Calif.). DAPI and DNAse were obtained from Sigma Aldrich (St. Louis, Mo.). Anti phosphotyrosine, 4G10 and goat anti-mouse antibody were obtained from Upstate Cell Signaling Solutions (Lake Placid, N.Y.). Anti-mouse TREM-2 antibodies (237920) for flow cytometry and (237916) for western blot analysis were purchased from R&D systems (Minneapolis, Minn.). Rabbit antibodies against PLC γ$_1$ (MC490), and DAP12 (MC457) were developed by Dr. Paul Leibson, Mayo Clinic. Ovalbumin labeled with FITC or APC was purchased from Molecular Probes (Eugene, Oreg.). Protein A Sepharose was purchased from Pierce Biotechnology (Rockford, Ill.). All inhibitors were obtained from Calbiochem (San Diego, Calif.) unless otherwise indicated. Piceatenol was obtained from Sigma Aldrich. Rac-1 inhibitor, NSC23766 was a gift from Dr. Daniel Billadeau, Mayo Clinic. LPS was obtained from Sigma Aldrich. CpG oligonucleotides were synthesized at the Mayo core facility. The polynucleotide pI:C was purchased from Calbiochem (San Diego, Calif.). All MTABs were purified as described (Warrington et al. (2000), supra) and used at 10 µg/ml.

Generation of Mixed Glial Cultures:

Oligodendrocytes from rat pups were obtained as per the protocol previously described (Warrington et al. (2000), supra). Briefly, tissue culture plates coated with poly-D-lysine (25 ug/mL) prepared in water for 1-2 hours at 37° C. were used for culturing the cells. Rat pup brains were removed under sterile conditions. Cerebral hemispheres, hindbrain, cerebella, thalamus, hippocampus, and meninges were removed and minced into 1 mm chunks with a sterile single-edge razor blade. Tissue chunks were trypsinized, subjected to shaking for 30-40 minutes at 37° C., and heat inactivated fetal calf serum was added to a final concentration of 10% to inactivate the trypsin. DNAse at 1:50 was added to the solution and incubated for 5-10 minutes. This process was repeated until a single cell suspension was achieved. The cell suspension was layered over a cushion of 4% BSA and then centrifuged. Supernatant was collected and the cells were resuspended in DMEM containing 10% FCS at a density of $20 \times 10^7$ cells/plate. Media was changed 4 days post-seeding and every 3 days thereafter. The plates were shaken at day 9 to obtain a heterogenous population of oligodendrocytes.

Production of shTREM2 and shControl Virus:

Oligos containing the shTREM2 sequence (5'-TGAT-GCTGGAGATCTCTGGGTTCAAGAGACCCAGA-GATCTCCAGCATCTTTTTC-3; SEQ ID NO:1) and shControl sequence (5'-TGACTGCTGAAGGTCGCTT-GTTTCAAGAGACCAAGCGACCTCCAG-CATCTTTTTC-3'; SEQ ID NO:2) (Warrington et al. (2000), supra) were synthesized and cloned into the pSU-PER RNAi System (provided by Dr. Daniel Billadeau, Mayo Clinic) using the key restriction sites Bgl II and Hind III. The sequence was confirmed by automated sequencing of the vectors. The resulting vectors were co-transfected with VSV-G and gagpol plasmids (both provided by Dr. Richard Vile, Mayo Clinic) into 293T cells. Supernatant was collected at 48 and 72 hours, pooled, filtered through a 0.45 micron filter and frozen until used for transduction.

Immunoblots:

In experiments involving assessment of the phosphorylation status of various protein kinases using whole cell lysate, dendritic cells of mouse or human origin or Jurkat cells were stimulated at the indicated times with control antibody or B7-DC XAb, and were lysed on ice for 10 minutes in 1 ml buffer containing 20 mM Tris-HCl, 40 mM NaCl, 5 mM EDTA, 50 mM NaF, 30 mM $Na_4P_2O_7$, 0.1% BSA, 1 mM $Na_3VO_4$, 1 mM PMSF, 5 µg/ml aprotinin, 10 µg/ml leupeptin, and 1% Triton X-100. Cellular debris was removed by centrifugation at 20,800×g for 5 minutes at 4° C. and the supernatant was used in SDS-PAGE analysis for phosphorylated tyrosine proteins. Protein complexes were eluted in 40 µl of SDS sample buffer, resolved by SDS-PAGE, and transferred to Immobilon-P membranes (Millipore). Tyrosine-phosphorylated proteins were detected using the anti-phosphotyrosine specific antibody, 4G10, followed by goat anti-mouse IgG coupled to Horse Radish Peroxidase (Santa Cruz Biotechnology) and the SuperSignal detection system (Pierce Biotechnology, Rockford, Ill.). Thereafter, total protein was visualized by staining the membrane with Ponceau staining solution (Pierce Biotechnology) for 30 seconds for analysis of whole cell lysate. For immunoprecipitation assays, the membrane was stripped with 7M guanidine, blocked with BSA, and probed with the antibody against the whole protein followed by protein A coupled to HRP (Amersham Biosciences) and the SuperSignal detection system. For pull down assays from the macro molecular complex, affinity purified antibody against mouse Class II (I-A$^b$) (KH74) was used for immunoprecipitation. The supernatants were resolved by SDS-PAGE, probed with anti-mouse TREM-2 antibody (237920) and detected by Goat-anti mouse antibody coupled to HRP, or probed with affinity purified anti-mouse CD40 (1C10) and detected by Goat-anti mouse antibody coupled to HRP.

Live Cell Imaging for Visualization of Macromolecular Complex:

Jurkat cells were pre stained with anti-human CD28-FITC (CD28.2) for 15 minutes, followed by addition of 10 µg/ml of MTAb control antibody sHIgM39, MTAb sHIgM22, or anti-K$^b$ IgM (28-13-3).

Flow Cytometry and FRET:

The flow cytometry approach for FRET was used as a way of quantifying molecular aggregation on the cell surface and was carried out as described previously (Block et al. (2001) J. Immunol. 167:821-826). Jurkat cells were stained with anti-human Class I-PE (G46-2.6) or anti-human CD4 (RPA-T4) and anti-human CD28-APC (CD28.2) for 15 minutes. Cells were stimulated with control antibody or B7-DC XAb or purified anti-mouse class II IgM (25-9-3) (experiments involving DC) or sHIgM22 (experiments involving Jurkat cells) and aliquots from different groups were taken at different time points. After 15 minutes of incubation, the cells were washed and fixed in 2% paraformaldehyde prior to analysis by FACS using a FACSCALIBER™ (BD Biosciences, Franklin Lakes, N.J.). Data collected as $log_{10}$ fluorescence were analyzed using CELLQUEST™ (BD Biosciences). The FRET signal was visualized in FL3 channel (650-670 nm LP).

Phage Display Library:

A disulfide constrained heptapeptide phage display library from New England Biolabs (Ipswich, Mass.) was used for phage display (Felici et al. (1991) J. Mol. Biol. 222:301-310). The randomized sequence in the library is flanked by cysteine residues, allowing disulfide cross-link that results in phage display of cyclized peptides. Host strain ER2738 and phage titering were followed per New England Biolab's instruction manual. Briefly, a tissue culture dish was coated with 30 µg/ml of sHIgM22 in 2 ml of PBS overnight at 4° C. The following day, an exponential culture of ER2738 was grown in Tetracycline LB media. After blocking and washing, the phage library was diluted to $2 \times 10^{11}$ in 1 ml of 1×TBS containing Tween-20 buffer. Upon removal of unbound phage by repeated washing, bound phage was eluted with 1.5 ml of 0.2M Glycine pH 2.2. After neutralizing with 1M Tris pH 9.0, eluted phage was added to an exponentially growing culture of ER 2738 bacteria and was allowed to amplify for 4.5 hours at 37° C. PEG was used to precipitate the culture supernatant. After 4 rounds, the amplified phage was cloned by limiting dilution. Twenty single-phage containing colonies were picked for sequence analysis. A peptide sequence (5A) present in 7 of 20 colonies was identified.

Generation of K$^b$/L$^d$-5A Class I-Peptide Chimera:

The 5A consensus peptide (PPWQSWI; SEQ ID NO:3) coding sequence was introduced into the K$^b$/L$^d$ gene (Pullen et al. (1989) J. Immunol. 143:1674-1679) by site directed mutagenesis (Stratagene, Cedar Creek, Tex.) as per manufacturer instructions. Briefly, two complementary oligonucleotides were generated. The 5' strand included a sequence encoding the consensus 5A peptide (PPWQSWI; SEQ ID NO:3) flanked by a HSAC (SEQ ID NO:13) spacer on the 5' end and 20 bases of the K$^b$ intron sequence. The 3' end included a CG spacer followed by 20 bases of the alpha one domain of the class I gene. Oligonucleotides were isolated by PAGE purification. A mixture consisting of 290 ng of each oligo with 500 ng of 5A7-K$^b$ template DNA was amplified with Ultra HF polymerase for 18 cycles at 95° C. for 1 minute and 55° C. for 1 minute, followed by one cycle of elongation at 68° C. for 10 minutes. After treatment with the endonuclease DpnI, the samples were transformed into XL-10 competent cells and plated on Ampicillin plates, and 
12 randomly selected colonies were sequenced with ABI's 3730XL capillary sequencer. Positive colonies were grown up using Qiagen's Endotoxin Free Mega plasmid purification kit.

Transfection of Jurkat T cells: The day prior to transfection, plasmid DNA of each construct was purified by ethanol precipitation. Jurkat cells ($15 \times 10^6$ cells) were resuspended in 250 µl RPMI, and 50 µl of resuspended DNA was added. After 10 minutes of incubation at room temperature, the whole suspension was transferred to a #640 BTX 4 mm Gapped cuvette and electroporation was carried out at 315 volts, 1 pulse, 10 pulse length, and at low voltage using a BTX Model 820 electroporator. Cells ($1 \times 10^6$/ml) were resuspended in RPMI containing 10% FCS. After overnight incubation at 37° C., cells were harvested and used for assays.

Example 2

The delineation of signaling pathways of B7-DC XAb provides a basis for evaluating the mechanisms of activation employed by other MTAbs. The monoclonal MTAbs 04 (Asakura et al. (1998) J. Neurosci. 18:7700-7708) and rHIgM22 (Warrington (2000), supra; and Mitsunaga et al. (2002) FASEB J. 16:1325-1327) bind oligodendrocytes and induce remyelination of denuded axons when administered systemically to mice. Primary oligodendrocytes and oligoglial cell lines mobilize a calcium response when exposed to the MTAbs 04 and rHIgM22 (Pas Soldan et al. (2003) Mol. Cell. Neurosci. 22:12-24; and Howe et al. (2004) Neurobiol. Dis. 15:120-131). These strong parallels observed among cells activated with the MTAbs B7-DC XAb, 04, and rHIgM22 suggest a common mechanism of membrane rearrangement that leads to recruitment of signaling molecules into macromolecular caps, mobilizing specific tissue responses in vitro and vivo. The precise nature of the molecules mediating MTAb induced signals in oligodendrocytes remains undefined. Several different IgM antibodies share the ability to activate oligodendrocytes (Warrington et al. (2000), supra; Miller and Rodriguez, supra; Asakura et al., supra; Pas Soldan et al., supra; and Howe et al., supra). These antibodies appear to target more than one cell surface molecule, as indicated by blocking a cellular activation of one IgM by its IgG switch variant, but the inability of that IgG antibody to block cellular activation by other IgM antibodies that target the same cells (Howe et al., supra).

One hypothesis is that the MTAbs are targeted to cells by moderate specific binding affinity for molecules distinctly expressed by specific cell types. Once bound to these cell restricted epitopes, the antibodies may interact by secondary, weak cross-reactivity with other cell surface molecules that are moving on the membrane, drawing them into a tight cluster. The structure of the induced clusters may lead to activation of cell surface molecules with intrinsic signaling capability, initiating preprogrammed changes in cellular function.

To test this hypothesis, a molecule displaying low but measurable binding for the oligodendrocyte-specific MTAb rHIgM22 was engineered and introduced into Jurkat cells to serve as bait and attract the MTAb to the surface of a cell not normally targeted by the IgM antibody. To construct this antibody target, a phage display peptide library was screened to identify a peptide mimetope that binds weakly to the remyelinating antibody sHIgM22. The peptide sequence was incorporated into the coding sequence for the N-terminus of a $K^b/L^d$ chimeric mouse class I molecule (Pullen et al. (1989) *J. Immunol.* 143:1674-1679) and the gene was expressed in human Jurkat T cells by transient transfection. Previous studies had demonstrated that peptides introduced at the amino terminus of a mouse class I extracellular domain can be expressed without disrupting the expression and structural integrity of the class I molecule (Hedley et al. (1989) *J. Immunol.* 143:1026-1031). By introducing an artificial target capable of attracting rHIgM22 onto the surface of Jurkat cells, a signaling complex was assembled that resulted in activation of cellular tyrosine kinases. This experimental system validates the model, and demonstrates that two different MTAbs function by recruiting cell surface proteins to a macromolecular complex.

The concept that antibodies can modulate cell functions by their ability to bind cell surface receptors is well established (Sege and Peterson (1978) *Proc. Natl. Acad. Sci. USA* 75:2443-2447; and Taub and Greene (1992) *Biochem.* 31:7431-7435). In addition to specific engagement of receptors by antibodies raised by direct immunization, observed interactions between naturally-occurring autoreactive antibodies and cells have given rise to the notion that natural antibodies may function as ligands supporting normal development and homeostatic maintenance of tissue physiology (Ando et al. (1994) *J. Biol. Chem.* 269:19394-19398; Coutinho and Avrameas (1992) *Scand. J. Immunol.* 36:527-532; and Avrameas (1991) *Immunol. Today* 12:154-159). Until now, however, there has been little mechanistic insight into how antibodies might function in this way. IgM antibodies with their decavalent binding structure would seem to be natural cross-linkers, however, many studies using IgM antibodies have required secondary cross-linkers to assemble molecular caps. The molecules described herein represent a subset of naturally occurring IgM autoreactive antibodies that are highly somatically mutated, distinguishing them in some respect from traditional natural antibodies (Miller and Rodriguez (1995), supra; Asakura et al., supra; Mitsunaga et al., supra; and Van Keulen et al. (2006) *Clin. Exp. Immunol.* 143:314-321), that have the capacity to induce macromolecular caps and activate signaling pathways without secondary cross-linking.

The accumulating evidence leads to the prediction that IgM antibodies capable of specifically activating a wide variety of cells in the human body can be identified. Recently, an IgM antibody has been described that activates neurons in culture, promoting neurite outgrowth (Warrington et al. (2004) *J. Neuropathol. Exp. Neurol.* 63:461-473). The IgM antibodies already described from mice and human patients have tended to bind to equivalent cell types in rodents and humans (Warrington et al. (2000), supra), indicating that the recognized epitopes are evolutionarily conserved structures. These shared products are likely the products of enzymatic modification of surface molecules. This cross-species reactivity demonstrates the potential clinical application of MTAbs using animal models of multiple sclerosis, cancer, and asthma (Warrington et al. (2000), supra; Miller et al. (1997) *J. Neuroimmunol.* 75:204-209; and Bieber et al. (2002) *Glia* 37:241-249). An important feature of the human MTAbs is that they were identified in patients with high titer monoclonal gammopathies. While each of these patients has high titers of IgM antibody in their serum, none of them have developed antibody-associated pathologies causing abnormal kidney, liver, cardiovascular, or neurologic functions. By identifying MTAbs from monoclonal gammopathy patients who are free of these antibody-associated pathologies, one can select IgM antibodies for further development that may behave well as therapeutic agents when administered to patients. Once MTAbs are identified in patient serum and tested for therapeutic activity using animal models of disease, recombinant sources of antibody can be generated using reverse genetics, as described previously (Mitsunaga et al., supra; and Van Keulen et al., supra), and prepared as GMP-grade reagents for clinical study.

Example 3—A Surrogate Target System for Investigation of Human MTAbs

A phage display system (Ph.D.-C7C Peptide Library Kit, New England Biolabs) was used to select 7-mer peptides in a cysteine loop for either hIgM12 or hIgM22. Briefly, a random peptide bacteriophage library was panned against immobilized antibody. Unbound bacteriophage was washed away, and bound bacteriophage was eluted, regrown and re-panned against the antibody. Multiple (three to seven) rounds of panning led to development of a peptide consensus sequence for each antibody. Two similar consensus sequences were identified for hIgM22, while one consensus sequence was identified for hIgM12 (Table 1).

TABLE 1

Amino acid sequences of consensus peptide targets

| Name | Sequence | No. of clones | SEQ ID NO: |
|---|---|---|---|
| hIgM22 peptides | | | |
| 22p3 | CPSEHQWIC | 4x | 14 |
| 22p5a | CPPWQSWIC | 7x | 15 |
| hIgm12 peptides | | | |
| 12p4 | CARNSTPPC | 1x | 16 |
| 12p9a | CHQTEKLTC | 11x | 17 |

Peptides 22p3 and 12p9A, which represented 4 and 11 clones, respectively, were selected. Each peptide was joined to the N-terminal sequence of the mouse MHC I molecule Kb with an Asp-Ser-Ala linker, permitting surface expression of the peptide. Kb was chosen due to its high level surface expression, previous work showing that peptides could be attached to Kb's N terminus without disrupting its structure, and possession of an anti-Kb IgM (28-13-3). In addition, a Kb construct with both peptides was constructed, with 22p3 N-terminal to 12p9A.

Kb, Kb-12p9A, Kb-22p3, and Kb-22p12p were placed in a VSV-G pseudotyped pBabe Puro retroviral vector, a vector based on the Maloney Murine Retrovirus. Previous experiments had shown that a high rate of transduction can be achieved, as measured by GFP expression, and that infection with the retrovirus does not alter the gross biology of DCs. Retrovirus was produced by transient transduction of 293T cells, and supernatant was concentrated 100:1 by ultracentrifugation on a 10% sucrose cushion. The retrovirus was titered with a colony forming unit assay of HT-1080 cells transduced with limiting dilutions of the supernatant concentrate, followed by selection with 2 ug/mL puromycin. Knockouts transduced with Kb did not respond to any antibody, while those transduced with the Kb-peptide constructs responded only to the appropriate antibody—hIgM12 when expressing Kb-12p9A and hIgM22 when expressing Kb-22p3.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A chimeric polypeptide comprising a first amino acid sequence and a second amino acid sequence, wherein the first amino acid sequence comprises an MEW Class I peptide Kb amino acid sequence, and where the second amino acid sequence comprises an epitope to which a multivalent molecule binds, wherein the multivalent molecule is an IgM antibody hIgM22 and the second amino acid sequence comprises SEQ ID NO: 3.

2. A linker molecule for targeting IgM antibody hIgM22 to a cell in the oligodendrocyte lineage, wherein the linker molecule is a polypeptide comprising (i) an amino acid sequence SEQ ID NO: 3 comprising an epitope to which hIgM22 specifically binds and (ii) an amino acid sequence that binds specifically to an epitope or marker on the surface of the cell in the oligodendrocyte lineage.

3. The linker molecule of claim 2 wherein the cell is an oligodendrocyte.

* * * * *

SEQUENCE LISTING

```
<160> NUMBER OF SEQ ID NOS: 17

<210> SEQ ID NO 1
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 1
tgatgctgga gatctctggg ttcaagagac ccagagatct ccagcatctt ttttc          55

<210> SEQ ID NO 2
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 2
tgactgctga aggtcgcttg tttcaagaga ccaagcgacc tccagcatct tttttc         56

<210> SEQ ID NO 3
<211> LENGTH: 7
<212> TYPE: PRT
<213> ORGANISM: Artificial Sequence
<220> FEATURE:
```

<223> OTHER INFORMATION: synthetic polypeptide

<400> SEQUENCE: 3

Pro Pro Trp Gln Ser Trp Ile
1               5

<210> SEQ ID NO 4
<211> LENGTH: 106
<212> TYPE: PRT
<213> ORGANISM: Homo sapien

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Leu Arg Ser Gly Val Pro Ser Arg Phe Ser Gly Ser
    50                  55                  60

Gly Ser Gly Thr Asp Phe Thr Leu Thr Val Ser Ser Leu Gln Pro Glu
65                  70                  75                  80

Asp Phe Ala Thr Tyr Tyr Cys Gln Gln Ser Tyr His Thr Pro Trp Thr
                85                  90                  95

Phe Gly Gln Gly Thr Lys Val Glu Ile Lys
            100                 105

<210> SEQ ID NO 5
<211> LENGTH: 107
<212> TYPE: PRT
<213> ORGANISM: Homo sapien

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 6
<211> LENGTH: 118
<212> TYPE: PRT
<213> ORGANISM: Homo sapien

<400> SEQUENCE: 6

Gln Val Gln Leu Gln Glu Ser Gly Pro Gly Leu Leu Lys Pro Ser Glu
1               5                   10                  15

Thr Leu Ser Leu Thr Cys Thr Val Ser Gly Gly Ser Val Ser Leu Tyr
            20                  25                  30

```
Tyr Trp Ser Trp Ile Arg Gln Ser Pro Gly Lys Glu Pro Glu Trp Ile
         35                  40                  45

Gly Tyr Ile Tyr Ser Ser Gly Ser Thr Asp Tyr Asn Pro Ser Leu Arg
 50                  55                  60

Ser Arg Val Thr Ile Ser Leu Asp Thr Ser Asn Asn Arg Phe Ser Leu
65                  70                  75                  80

Asn Leu Arg Ser Val Thr Ala Ala Asp Thr Ala Val Tyr Trp Cys Ala
                 85                  90                  95

Arg Ser Ala Ser Ile Arg Gly Trp Phe Asp Pro Trp Gly Gln Gly Thr
            100                 105                 110

Leu Val Thr Val Ser Ser
            115
```

<210> SEQ ID NO 7
<211> LENGTH: 104
<212> TYPE: PRT
<213> ORGANISM: Homo sapien

<400> SEQUENCE: 7

```
Gly Ser Ala Ser Ala Pro Thr Leu Phe Pro Leu Val Ser Cys Glu Asn
 1               5                  10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
             35                  40                  45

Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                 85                  90                  95

Lys Glu Lys Asn Val Pro Leu Pro
            100
```

<210> SEQ ID NO 8
<211> LENGTH: 112
<212> TYPE: PRT
<213> ORGANISM: Homo sapien

<400> SEQUENCE: 8

```
Val Ile Ala Glu Leu Pro Pro Lys Val Ser Val Phe Val Pro Pro Arg
 1               5                  10                  15

Asp Gly Phe Phe Gly Asn Pro Arg Lys Ser Lys Leu Ile Cys Gln Ala
                20                  25                  30

Thr Gly Phe Ser Pro Arg Gln Ile Gln Val Ser Trp Leu Arg Glu Gly
             35                  40                  45

Lys Gln Val Gly Ser Gly Val Thr Thr Asp Gln Val Gln Ala Glu Ala
 50                  55                  60

Lys Glu Ser Gly Pro Thr Thr Tyr Lys Val Thr Ser Thr Leu Thr Ile
65                  70                  75                  80

Lys Glu Ser Asp Trp Leu Ser Gln Ser Met Phe Thr Cys Arg Val Asp
                 85                  90                  95

His Arg Gly Leu Thr Phe Gln Gln Asn Ala Ser Ser Met Cys Val Pro
            100                 105                 110
```

<210> SEQ ID NO 9
<211> LENGTH: 106

```
<212> TYPE: PRT
<213> ORGANISM: Homo sapien

<400> SEQUENCE: 9

Asp Gln Asp Thr Ala Ile Arg Val Phe Ala Ile Pro Pro Ser Phe Ala
 1               5                  10                  15

Ser Ile Phe Leu Thr Lys Ser Thr Lys Leu Thr Cys Leu Val Thr Asp
            20                  25                  30

Leu Thr Thr Tyr Asp Ser Val Thr Ile Ser Trp Thr Arg Gln Asn Gly
        35                  40                  45

Glu Ala Val Lys Thr His Thr Asn Ile Ser Glu Ser His Pro Asn Ala
50                  55                  60

Thr Phe Ser Ala Val Gly Glu Ala Ser Ile Cys Glu Asp Asp Trp Asn
65                  70                  75                  80

Ser Gly Glu Arg Phe Thr Cys Thr Val Thr His Thr Asp Leu Pro Ser
                85                  90                  95

Pro Leu Lys Gln Thr Ile Ser Arg Pro Lys
            100                 105

<210> SEQ ID NO 10
<211> LENGTH: 131
<212> TYPE: PRT
<213> ORGANISM: Homo sapien

<400> SEQUENCE: 10

Gly Val Ala Leu His Arg Pro Asp Val Tyr Leu Leu Pro Pro Ala Arg
 1               5                  10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
        35                  40                  45

Pro Leu Ser Pro Glu Lys Tyr Val Thr Ser Ala Pro Met Pro Glu Pro
50                  55                  60

Gln Ala Pro Gly Arg Tyr Phe Ala His Ser Ile Leu Thr Val Ser Glu
65                  70                  75                  80

Glu Glu Trp Asn Thr Gly Glu Thr Tyr Thr Cys Val Val Ala His Glu
                85                  90                  95

Ala Leu Pro Asn Arg Val Thr Glu Arg Thr Val Asp Lys Ser Thr Gly
            100                 105                 110

Lys Pro Thr Leu Tyr Asn Val Ser Leu Val Met Ser Asp Thr Ala Gly
        115                 120                 125

Thr Cys Tyr
    130

<210> SEQ ID NO 11
<211> LENGTH: 337
<212> TYPE: DNA
<213> ORGANISM: Homo sapien

<400> SEQUENCE: 11
gacatccaga tgacccagtc tccatcctcc ttgtctgcgt ctgtaggaga cagagtcacc      60
atcacttgcc gggcaagtca gagtattagt agttatctaa attggtatca gcagaaacca    120
gggaaagccc ctaaggtcct gatctatgct gcatccactt tgcgaagtgg ggtcccgtca    180
aggttcagtg gcagtggatc tgggacagat ttcactctca ccgtcagcag tctgcaacct    240
gaagattttg caacttacta ctgtcaacag agttaccata ccccgtggac gttcggtcag    300
```

```
gggaccaagg tggaaatcaa acgaactgtg gctgcac                              337
```

<210> SEQ ID NO 12
<211> LENGTH: 369
<212> TYPE: DNA
<213> ORGANISM: Homo sapien

<400> SEQUENCE: 12

```
caggtgcagc tgcaggagtc gggtccagga ctgctgaagc cttcggagac cctgtccctc      60
acatgcactg tctctggtgg ctccgtcagt ctttactact ggagctggat ccggcagtcc     120
ccagggaagg aaccggagtg gattggatat atctattcca gtggaagcac cgattacaac     180
ccttccctca ggagtcgagt caccatatca ctggacacgt caaacaaccg gttttcccta     240
aacctgaggt ctgtgaccgc cgcagataca gcggtctatt ggtgtgcgag aagtgcgtca     300
attaggggct ggttcgaccc ctggggccag ggaaccctgg tcaccgtctc ctcagggagt     360
gcatccgcc                                                             369
```

<210> SEQ ID NO 13
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 13

```
His Ser Ala Cys
1
```

<210> SEQ ID NO 14
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 14

```
Cys Pro Ser Glu His Gln Trp Ile Cys
1               5
```

<210> SEQ ID NO 15
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 15

```
Cys Pro Pro Trp Gln Ser Trp Ile Cys
1               5
```

<210> SEQ ID NO 16
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 16

```
Cys Ala Arg Asn Ser Thr Pro Pro Cys
1               5
```

<210> SEQ ID NO 17
<211> LENGTH: 9

```
<212> TYPE: PRT
<213> ORGANISM: Artificial Sequence
<220> FEATURE:
<223> OTHER INFORMATION: synthetic polypeptide

<400> SEQUENCE: 17

Cys His Gln Thr Glu Lys Leu Thr Cys
1               5
```